United States Patent [19]

Kawaguchi et al.

[11] Patent Number: 5,148,022
[45] Date of Patent: Sep. 15, 1992

[54] METHOD FOR OPTICALLY INSPECTING HUMAN BODY AND APPARATUS FOR THE SAME

[75] Inventors: Fumio Kawaguchi, Tokyo; Hiroshi Takeuchi, Matsudo; Yasuhiro Mitsui, Fuchu; Yoshitoshi Ito, Ome; Munetaka Haida, Isehara, all of Japan

[73] Assignee: Hitachi, Ltd., Tokyo, Japan

[21] Appl. No.: 479,171

[22] Filed: Feb. 13, 1990

[30] Foreign Application Priority Data

Feb. 15, 1989 [JP] Japan .................. 1-035441

[51] Int. Cl.⁵ .............................................. G01N 21/59
[52] U.S. Cl. ........................................ 250/341; 250/339
[58] Field of Search ............................... 250/339, 341

[56] References Cited

U.S. PATENT DOCUMENTS

| | | | |
|---|---|---|---|
| 4,449,535 | 5/1984 | Renault | 128/634 |
| 4,515,165 | 5/1985 | Carroll | 250/341 X |
| 4,767,928 | 8/1988 | Nelson et al. | 250/341 |
| 4,773,097 | 9/1988 | Suzaki | 382/6 |
| 4,798,955 | 1/1989 | Rosenthal | 250/341 |
| 4,805,623 | 2/1989 | Jöbis | 128/633 |
| 4,945,239 | 7/1990 | Wist et al. | 250/358.1 |

FOREIGN PATENT DOCUMENTS

| | | |
|---|---|---|
| 0099756 | 7/1983 | European Pat. Off. |
| 0140633 | 10/1984 | European Pat. Off. |
| 0222555 | 10/1986 | European Pat. Off. |
| 0298122 | 11/1987 | European Pat. Off. |
| 0280986 | 2/1988 | European Pat. Off. |
| 0290279 | 5/1988 | European Pat. Off. |
| 60-072542 | 4/1985 | Japan. |
| 63-115548 | 5/1988 | Japan. |
| 63-206655 | 8/1988 | Japan. |
| 1-88340 | 4/1989 | Japan .................. 250/339 |
| 8801485 | 3/1988 | World Int. Prop. O. |

Primary Examiner—Constantine Hannaher
Attorney, Agent, or Firm—Antonelli, Terry, Stout & Kraus

[57] ABSTRACT

A method for optically inspecting a human body and an apparatus for the same serve to scan a light pulse having a visible wavelength to an infrared one on a specific sliced portion of a body to be inspected, for obtaining pieces of projection data about light absorption and to reconstruct an image about distribution of light absorption from the projection data with a computer tomogram. The projection data is measured by alternately radiating a first light pulse at a first wavelength in an absorption wavelength band specific to metabolic materials to be imaged and a second light pulse at a second wavelength being closer to said first wavelength. Then, the data about the transmitted beams are produced by deriving a ratio of integrated values of the first signal to the second one residing within a specific time gate.

16 Claims, 6 Drawing Sheets

METHOD FOR OPTICALLY INSPECTING HUMAN BODY AND APPARATUS FOR THE SAME

BACKGROUND OF THE INVENTION

The present invention pertains to a medical or diagnostic inspecting method. More particularly, the invention is directed to the method and apparatus for non-invasively obtaining measured information about metabolism using light beams of visible to infrared wavelength.

Today, clinical medicine has attained to the point where various kinds of diseases can be diagnosed on measuring results about morphology of body organs. And, imaging systems for diagnosis use such as a supersonic diagnostic system and an X-ray CT scanner have been so progressive that they can detect morphologic abnormality entailed by diseases with considerable accuracy. In general, metabolic functions are diagnosed in vitro assay, though a positron CT scanner or MRI system provides a certain kind of metabolic function.

U.S. Pat. No. 4,281,645 on the other hand, describes a method and an apparatus for optically monitoring metabolism in body organs in vivo depending upon the fact that a certain kind of metabolic material contains specific optical absorption bands. The Japanese First Patent Publication No. 60-72542 (1985) describes a system for obtaining a tomogram, which indicates how metabolic materials are distributed in body organs. The system is designed to match each element included in the system for metabolic modeling to each element included in an X-ray CT scanner.

The Japanese First Patent Publication No. 63-115548 (1988) has proposed a method for eliminating a light-scattering phenomenon in the foregoing optical inspecting system. The scattered light mentioned in the art, however, means the light scattered by the materials external of the body, that is, "stray light" and the light reflected on the surface of a body to be inspected. Further, the Japanese First Patent Publication No. 63-206655 (1988) discloses a method of comprising the steps of dividing a light pulse into two, allowing one pulse to pass through a human body to be measured, introducing two pulses into crystals, the one as a sampling light and the other as a reference light, detecting second higher harmonics generated from the crystals, inhibiting detection of light scattered in the human body by referring the second higher harmonics, and detecting only the light transmitted through an optical path with a predetermined width.

SUMMARY OF THE INVENTION

The largest problem the conventional system for optically inspecting a human body involves resides on the fact that there is provided no essential information about how metabolic materials absorb light, because the light passed through a body organ is adversely effected by scattering of light in a body surface or several portions of the body rather than optical absorption of an imaging object, that is, the metabolic materials. It results in often making a tomogram unsatisfactory.

It is an object of the present invention to provide a method and an apparatus for optically inspecting a human body which is capable of more precisely extracting data about how the specific metabolism-related materials in a body to be inspected absorb light.

It is the other object of the present invention to provide a method and an apparatus for optically inspecting a human body which is capable of precisely setting a time gate depending on a form of a body organ to be inspected.

To measure distribution of a specific metabolism-related material in an organic body, the invention offers a method which comprises the steps of serially radiating to the material a first light pulse at a first wavelength residing within a characteristic absorption band of the material and a second light pulse at a second wavelength near the first one, allowing these two light pulses to pass through an organic body to specific light-receptacle spots, detecting at each specific spot each integrated value of quantity of light residing within each specific time gate, calculating a ratio of a first integrated value corresponding to the first incident light pulse to a second integrated value corresponding to the second incident light pulse, and employing the ratio as data for obtaining the distribution of a specific metabolic material. The two methods of taking such a time gate have been proposed. The first method is designed to control a high-speed optical shutter provided at each light-receptance spot with respect to a generation timing of each light pulse for passing light to an optical detector during a specific period. The second method is designed to sweep an optical output matching to each light pulse at high speed as it is recorded and calculate an integrated value in a specific time region of the output waveform (optical time spectrum). For the latter method, recording of an optical output wavelength can be realized by, what is called, a streak camera, which serves to lead the light detected at each light-receptacle spot into an optical cathode and sweep an electronic beam fired at the optical cathode to an optical anode by using the effect of an electric field.

Mentioning in detail, the foregoing measuring methods using two kinds of light pulses serve to change a radiating spot and light-receptance spots on a specific plane in succession. It results in offering projection data viewed from a plurality of angles about the difference of each absorption. Based on the projection data, a computer tomographic method serves to reconstruct a tomogram indicating how the metabolic materials in question are distributed in a body to be inspected. How to reconstruct a tomogram can employ various algorithms used in an X-ray CT scanner such as a convolution method and a one-dimensional Fourier transformation method. The former method comprises the steps of performing convolution integration with respect to each projection data as well as back projection with respect to the result. The latter one comprises the steps of performing Fourier transformation with respect to each projection data, multiplying the resulting value with a filter function in a space frequency domain, and performing reverse projecting operation using the multiplied value. Since the present invention employs a beam of light whose wavelength ranges from a visible one to an infrared one, however, the beam is subject to strong coherent light scattering in any spot of an organic material, unlike the X-ray beam. It means that the invention can offer no information about absorption of the metabolic material in question placed on an optical path if a light-receptance spot is placed along a light path and just in the rear of the body to be inspected, because light scattered on the body to be inspected is mingled into the beam of light. A certain kind of metabolic material such as cytochrome has a specific peak to an optical absorption spectrum, while no peak exists in a spectrum if light scattering is brought about in each portion of a body to be inspected containing the material. The foregoing measuring difference between two wavelengths, therefore, can be used for extracting data about light attenuation, which results from the fact that the metabolic material absorbs light. Further, by introducing a time gate for each wavelength, it is possible to eliminate the light deviated from the proper optical path, that is, refracted or reflected light and to extract a signal matching to only the light transmitted through a specific-width straight path. The present invention, therefore, can offer so resolutive a tomogram showing how metabolic materials are distributed that it can be used for medical diagnosis.

The time gate width is defined on a width of an optical path for absorption data. And, it is necessary to match a start time of the time gate to a light path length in an organic body. Before measuring the tomogram, therefore, it is necessary to measure a form of a slice to be inspected. For the measurement, there may be employed an optical detector for measuring projection data about absorption distribution or another imaging device such as an X-ray CT scanner or an MRI system.

DESCRIPTION OF THE PREFERRED EMBODIMENTS

Hereinafter, a description will be directed to one embodiment of the present invention with reference to the drawings.

Figure 1:
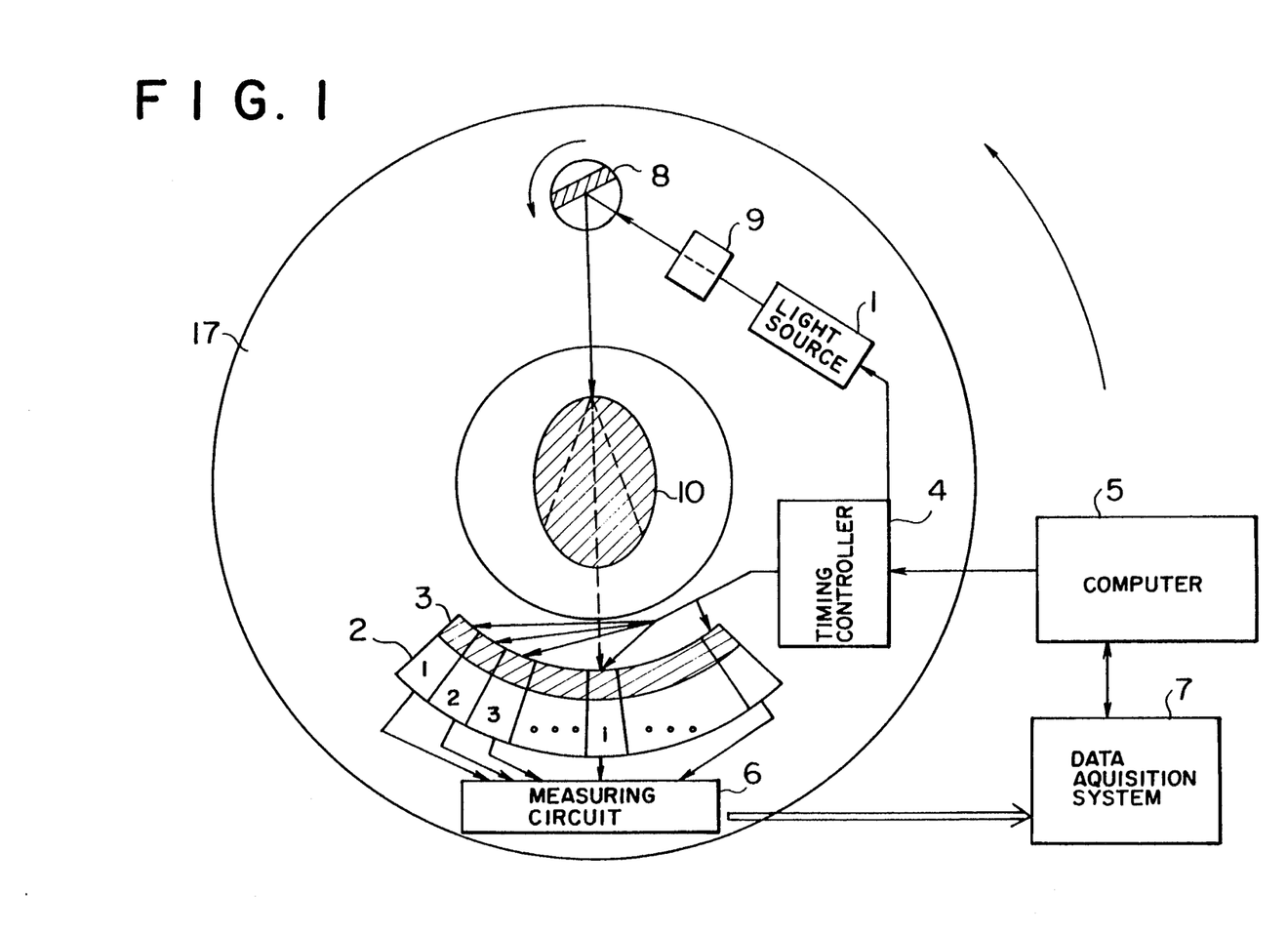
FIG. 1 is a block diagram showing arrangement of one embodiment according to the invention.

FIG. 1 is a block diagram showing an apparatus for optically inspecting a human body according to one embodiment of the invention. The apparatus is analogous to an X-ray CT scanner while utilizing a light source as the radiation source and an optical detector as the detector. It includes a similar scanning mechanism to the third-generation system X-ray CT scanner. As shown, an optical radiating section comprises a light source 1, an optical system, and a rotary mirror. The optical detecting section comprises the optical detector 2, an optical shutter, and a measuring circuit 6. These optical radiating section and optical detecting section are mounted on a rotary gantry 17. The gantry 17 has a central void into which a body to be inspected 10 is inserted. 4 denotes a timing controller for controlling the light source 1 and the light shutter 3, 7 denotes a data acquisition system for accumulating measured data, and 5 denotes a computer for processing the measured data accumulated in the data acquisition system 7 and controlling the timing controller 4 and the data acquisition system 7.

Next, the function of each portion will be set forth in detail.

The light source 1 consists of a laser-emitting apparatus which is capable of iteratively radiating a light pulse having a narrower time width. It can radiate two kinds of light pulses in an alternate manner. These light pulses have respective wavelengths. The light source 1, as stated above, has a function of iteratively radiating a light pulse having a time width of 100 picosecond or less to a body to be inspected 10 in accordance with an indication sent from the timing controller 4. The radiated laser beam has an alternate one of a first wavelength existing in a characteristic absorption band of metabolic materials, that is, an imaging object. For example, for measuring deoxyhemoglobin in blood, the used wavelengths are 760 nm, which is a characteristic absorption wavelength of this material, and the value approximating to it (e.g. 800 nm).

For removing the quantity of attenuation resulting from light scattering, it is necessary to measure the quantity of attenuation caused as a result of transmitting two light pulses at respective wavelengths and calculate a ratio between the measured attenuations. This is because if a difference between both wavelengths is quite small, both beams have the same quantity of attenuation resulting from light scattering.

Assume that a difference between two wavelengths is not made so small. For example, assume the case of the small difference between the wavelengths of the absorption spectrums in the organic material to be measured as well as the small difference of an absorption coefficient between the wavelengths closing to each other, thereby providing not so large difference of absorption attenuation between both wavelengths.

Under that condition, for removing an adverse effect of light scattering, it is preferable to employ the method of selecting two wavelengths whose absorption coefficients are different from each other, selecting one medium wavelength positioned between those two, radiating a total of three beams of light at respective wavelengths, measuring each, and calculating three measured values.

Furthermore, by measuring densities of deoxyhemoglobin and oxyhemoglobin and calculating a ratio between both densities, it is possible to obtain an oxygen saturation in hemogrobin. The oxygen saturation means how much oxygen is fed to body organs. It properly indicates a functional change of body organs. For the measurement, it is necessary to employ a specific wavelength of, for example, 650 nm in which an absorption coefficient is different in each hemoglobin and a wavelength of, for example, 850 nm in which an absorption coefficient is same in each one. For removing the foregoing adverse effect of light scattering, it is necessary to take the steps of extracting data measured by the light pulse with a wavelength of 650 nm and data measured by the light pulse with its wavelength approximating to the former, calculating a ratio of both data, extracting data measured by the light pulse with a wavelength of 850 nm and data measured by the light pulse with its wavelength approximating to the former, and calculating a ratio of both data. That is, the measurement requires a total of four light pulses with respective wavelengths.

According to this embodiment, it is preferable that the wavelength of a laser beam should range from 700 to 1300 nm, because the wavelength in the range hardly brings about light scattering in body organs and water absorption.

The optical system 9 has a function of shaping a beam radiated from the light source into parallel beams whose sections are small. The rotary mirror 8 is rotated depending on control of the computer 5. It operates to allow laser beams to scan an overall area of a body to be inspected 10. Hence, the overall process takes the steps of shaping the beam radiated from the light source 1 into parallel beams whose sections are small, reflecting the parallel beams on the rotary mirror and then entering into the body to be inspected 10.

Figure 2:
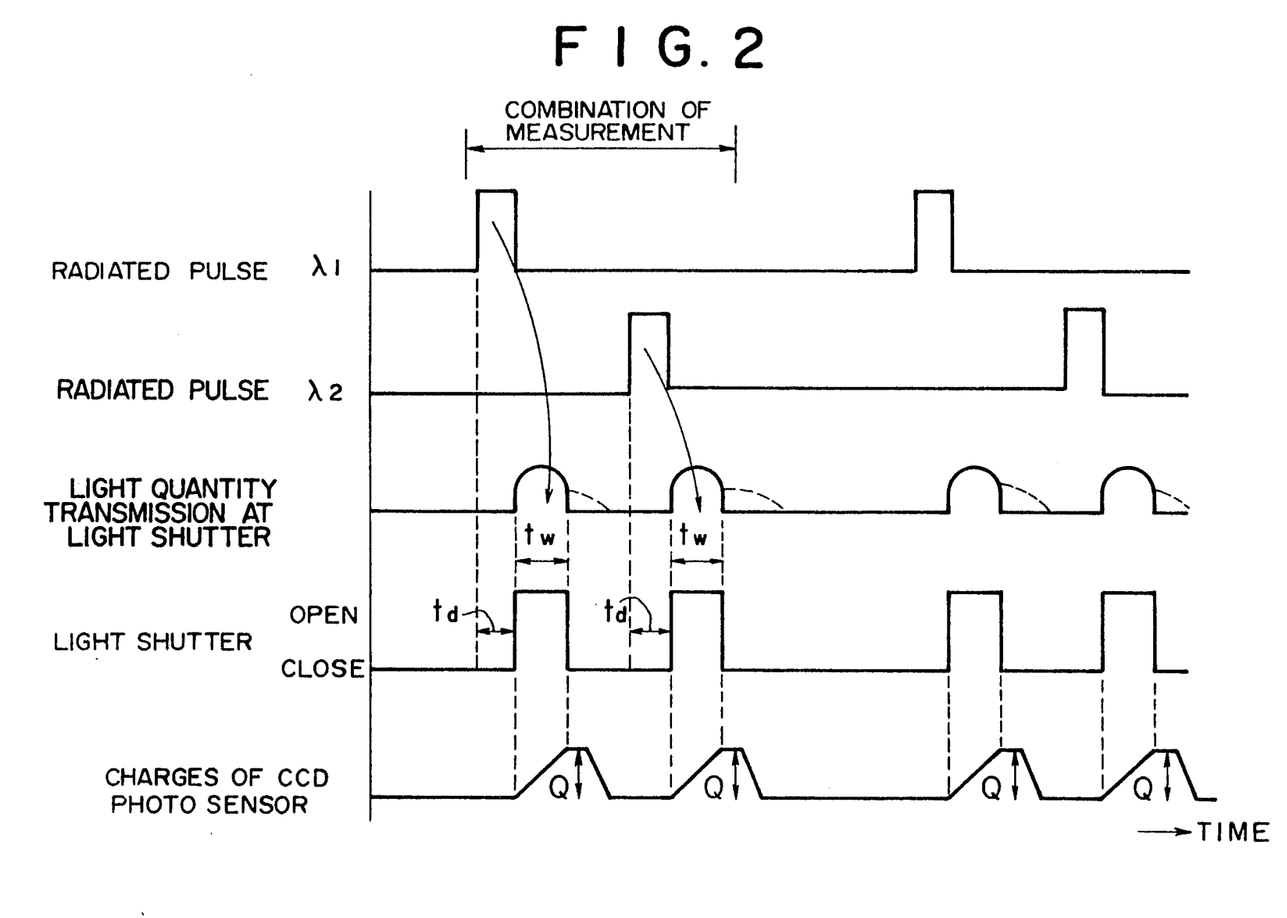
FIG. 2 is a time chart showing a measuring function according to the embodiment.

FIG. 2 shows a pulse of a radiated beam, switching of an optical shutter (to be described later), and one example of a signal waveform detected in an optical detector. As stated above, the beam is radiated in a manner to alternately switch two wavelengths ($\lambda_1$, $\lambda_2$). The basic unit of measurement is a pair of twice measurements done using these light pulses having respective wavelengths. As shown in FIG. 2, the light shutter 3 is opened later than a leading edge of a radiated light pulse by a timing $t_d$ (to be described later), keeps open for a width of $t_w$, and then is closed. This function enables only the light led to the optical detector for a set time to be selectively measured.

For using three light pulses having respective wavelengths, the basic unit of measurement is a combination of three or more times measurements.

The intensity of the light pulse in each measuring time is controlled by the computer 5 so that the quantity of radiated light becomes optimal. This control results in making all the quantity of radiated beam of light in each optical detector element substantially similar. When the light beam is radiated around the center of a body to be inspected, the quantity of radiated light is increased and the quantity of radiated light is diminished around the body to be inspected. This control is done on the data about the form of a body to be inspected, which has been measured in advance. Further, it is preferable to iteratively perform a combination of measurements in which the same optical detector elements detect light pulses with respective wavelengths and to average the measured results for heightening measuring accuracy.

Again, a description will be returned to the function of each part.

The optical detector 2 consists of arranged high-sensitivity optical detecting elements such as a CCD photo sensor. To measure a body organ to be inspected, the center of a light beam is directed onto the i-th optical detector element and the light pulses are radiated at respective wavelengths ($\lambda_1$, $\lambda_2$) one by one. The i-th optical shutter is opened for each light pulse so that the CCD photo sensor can condense a quantity of light received during a light-incident period as quantity of charges. Each time it finishes condensing, the measuring circuit 6 reads out the quantity of charges Q. It results in providing data indicating an integrated value of the light quantity given for an opening period. The data is provided serially for each pulse. A data acquisition system 7 serves to analog-to-digital convert two pieces of measuring data sent from the i-th element and then reserve them. It means that two pieces of data are provided for one measurement of one element. And, as stated above, more than one measurement may be performed using two wavelengths at the same spot. In this case, the measured data are averaged and the resulting pair of data are reserved.

The above-mentioned measurement is carried out about all the elements starting from an element of i=1. The resulting data is regarded as projection data at each degree of CT scanner. Next, like the three-generation X-ray CT scanner, the gantry 17 is rotated around the body to be inspected 10 by a predetermined angle and that measurement is done again. The 360° rotation of the overall detecting system results in the CT scanner offering all the data.

Next, the function of the optical shutter 3 will be described.

On the front surfaces (plane of incidence) of each detecting element are provided the individually-controllable optical shutter 3 matching to each element. The optical shutter 3 operates to allow light to be incident to the detector elements during a predetermined time gate width. In this embodiment, the optical shutter 3 is made of an electro-optical element to be rapidly operated such as Kerr shutter made of $CS_2$ crystal. The timing controller 4 serves to open only the optical shutters for the detector elements matching to the central axis of the radiated beam on the most approximate timing and keep the other elements closed in accordance with an indication sent from the computer 3. The opening or closing timing, that is, switching one is set as the most approximate time value obtained from a radial form (thickness of light passage) measured in advance.

Figure 3:
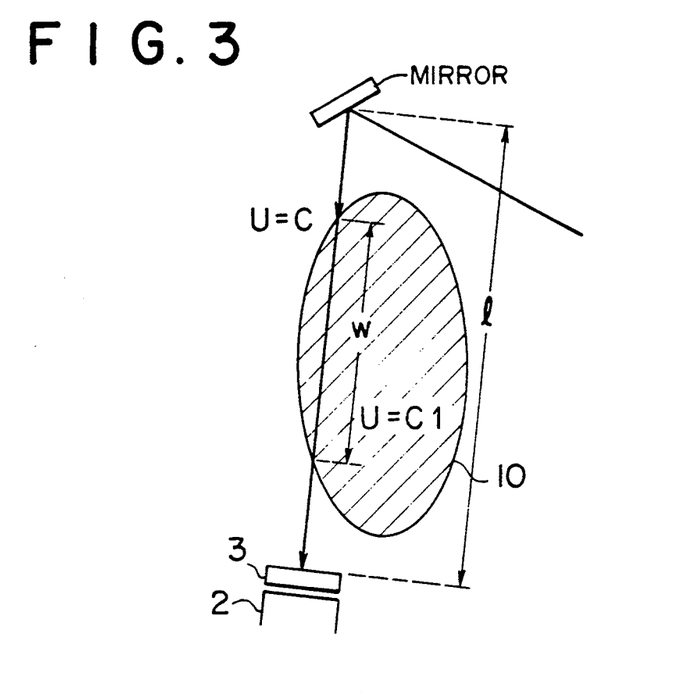
FIG. 3 is a sectional view showing a setting method of a time gate.

Then, a description will be directed to the switching timing of the optical shutter with reference to FIG. 3. Assuming that a light beam is radiated to a real-line spot on the body to be inspected 10, the following equation gives a minimum value $t_d$ of a time lag of the beam from the light source to the detector elements opposite to the spot.

$$t_d = (l-w)/c + w/C_1 + t_p \qquad (1)$$

where l denotes a distance between a rotary mirror plane and an optical detector; w denotes a distance of a portion of a body to be inspected through which a light beam passes; c denotes a light speed in the air; $c_1$ denotes a light speed in a body to be inspected; and $t_p$ denotes a time requiring a beam to lead from a light source to the rotary mirror plane.

Assuming the leading edge of a light pulse as a time origin, a signal light does not reach the optical detector before a time $t_d$. The incident light before the time means noises. l and $t_p$ are constant values, which are individually defined to each device. Hence, a value of $t_d$ can be calculated by deriving W at each optical path position based on a form of a body to be inspected. Hence, the light shutter 3 should be opened at a time point delayed by $t_d$ from the leading edge of a light pulse. Most of incident light reaches the light shutter 3 later than the time $t_d$, because light scattering is caused while the beam passes through the body to be inspected. The delay time is variable according to the width (w) of the area through which light passes. That is, as light deviates from the center of the light beam farther, its passing distance becomes longer. If light reaches the light shutter 3 in time ($t_d < t < t_d + t_w$), it is certain that the light passes through the defined area around the central axis of the light beam. By setting an "opening" time area of the light shutter 3 as $t_d - t_d + t_w$, therefore, it is possible to selectively pick up only the light passed through the defined area around the central axis of the light beam. This makes it possible to remove the adverse effect resulting from light scattering, exclude greatlyrefracted light, and define the area through which light passes, resulting in enabling the image reconstructing system using the conventional CT algorithms to be applied to this embodiment.

Figure 4:
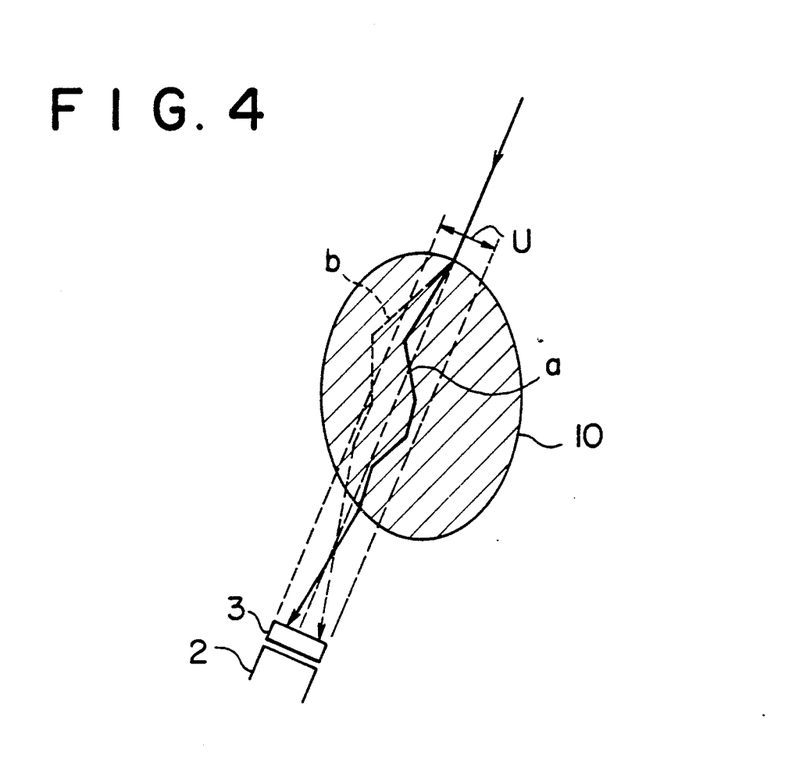
FIG. 4 is a sectional view showing effects of a time gate.

Given a time gate width $t_w$, the light b deviated from the area of a width U as shown in FIG. 4 requires a longer time than the time $t_w$ to reach the light shutter 3. On the other hand, the light a passing through the area of the width W is allowed to pass through the light shutter 3 for the time $t_w$. By setting the time $t_w$, therefore, it is possible to define the width of an area through which the incident light to the optical detector 2 passes. For setting the width U of the passing area as, for example, 10 mm, the time $t_w$ should be set as a value of several tens picoseconds. $t_w$ can be calculated using the equation of $t_w = U/c_1$, $c_1 = 3 \times 10^8/1.3$ (m/second) $= 2.3 \times 10^8$ (m/sec). The time gate width $t_w$ can be defined on the width U of a light-passing area. As $t_w$ is made smaller, U becomes smaller. Yet, since it is necessary to detect minute transmitted light on a high S/N ratio, $t_w$ should be defined as a larger value than a pulse width of a radiated light pulse. The response for several tens picoseconds can be realized by the foregoing Kerr shutter.

As noted above, in order to set a time gate with the light shutter, remove scattered light, and define a light-passing area, it is necessary to obtain data about a light flight distance in a body to be inspected and a light speed therein in advance. For obtaining the data, the apparatus for optically inspecting a human body according to the present embodiment is designed to measure a form of each body to be inspected and then how metabolic materials are distributed in a body to be inspected. Hereinafter, one example will be described.

At first, the measurement takes the steps of; placing a body to be inspected at the center of this apparatus; keeping all the light shutters 3 located in front of the optical detector 2 open, performing light scanning like a CT scanner, and detecting projections indicating an outer form or shape of the body to be inspected. It means that as the mirror 8 varies in angle for scanning a laser beam in the range of a fixed angle, each detector elements composing the optical detector serve to serially scan light attenuation resulting from the body to be inspected. It results in providing projection data indicated by a binary digit of "0" and "1". The above-mentioned measurement is repeated in several angles as the gantry 17 is rotated. On the other hand, the data acquisition system 7 serves to overlap a fan shape including projections viewed from several angular positions of the light source (mirror) on a two-dimensional memory on the basis of AND logic. The memory, therefore, leaves data indicating a section form of an object to be inspected on itself.

From the section form of the body to be inspected, it is possible to calculate a length of a light path in the body. For the calculation, a simple geometry is used. The light speed in the body to be inspected may approximate to the light speed in water, because a human body contains about 70% water. The speed $c_1$ has the following value;

$$c_1 = c/1.3 \text{ (1.3 is an index of refraction of water)}$$

From the length of light path in the body to be inspected and the light speed $c_1$ obtained by the above process, a setting value $t_d$ of the optimal time gate can be derived using the foregoing equation (1). A sectional form of the body to be inspected, which has measured in advance by the X-ray CT scanner, makes a contribution to setting a gate time so minutely as being matched to a light speed in each body organ.

Figure 5:
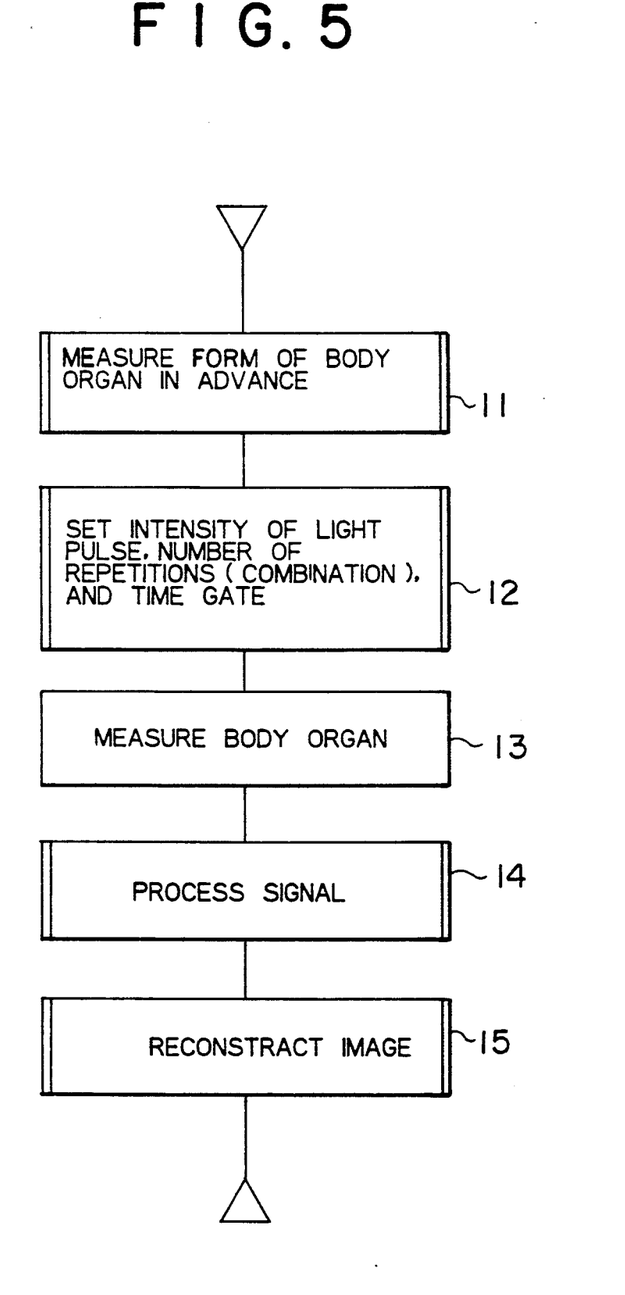
FIG. 5 is a flowchart showing measuring a function according to the embodiment.

Hereinafter, a description will be directed to how the foregoing measuring apparatus takes the measuring steps with reference to FIG. 5.

The measuring steps take the following steps of; measuring a sectional form of a body to be inspected in advance with a light beam or X ray (step 11); setting an intensity of a light pulse, a number of repetitions (pair), a time gate of the optical detector and the like (step 12); after completing setting of these values, measuring the body to be inspected with the light pulse (step 13); deriving projection data from the measuring data signal with a computer (step 14); and reconstructing an image to be outputted to a display (not shown) (step 15).

In the foregoing data processing, assuming that $x_{i1}$, $x_{i2}$ (i denotes a number of the optical detector) denote signals matching to the two light pulses with H respective wavelengths ($\lambda_1$, $\lambda_2$), it is necessary to derive a ratio of these signals;

$$A_i = x_{i1}/x_{i2}$$

where $A_i$ is generally derived by taking the logarithm of $x_{i1}$ and $x_{i2}$ and subtracting the latter from the former. The derived $A_i$ value indicates light attenuation, which results from light absorption caused when the beam passes through a band area defined by the time gate. This is because both beams are subject to the substantially same light scattering in a scattering material if the difference between their wavelengths is small (in actual, several tens nm). That is, both beams having respective wavelengths $\lambda_1$ and $\lambda_2$ are subject to similar attenuation resulting from light scattering, but are subject to only the effect resulting from the difference between their absorption coefficients. The output thus reflects only the difference. The above-mentioned measurement using all the detector elements results in providing, what is called, projection data given in the third-generation X-ray CT scanner. As the gantry rotates the combination of the detector and the light source little by little, the foregoing measurements are repeated for obtaining pieces of projection data. Then, using the algorithm of the CT scanner, the image reconstruction is performed for providing a distribution image of the absorptive material. As a representative example of image reconstruction, it comprises the steps of performing convolution integration about each piece of projection data as well as back projection about the resultants. As another example, it comprises the steps of performing primary Fourier transformation about each piece of projection data, multiplying the resultants by a filter function in a space frequency domain, performing reverse Fourier transformation about the multiplied values, and performing back projection about the resultants. Any one of them may employ a method of transforming each piece of projection data into projection data measured by parallel beams and performing image-reconstructing processing about the projection data or a method of performing an operation referred to as fan reverse projection method about the original projection data, that is, the data measured by a scanning method for a fan-like area. These methods are known as algorithms used in an X-ray CT scanner.

The embodiment as mentioned above may implement a method and an apparatus for eliminating an adverse effect resulting from light scattering in a body to be inspected and imaging the structure inside of a human body organ with a beam of light.

Figure 6:
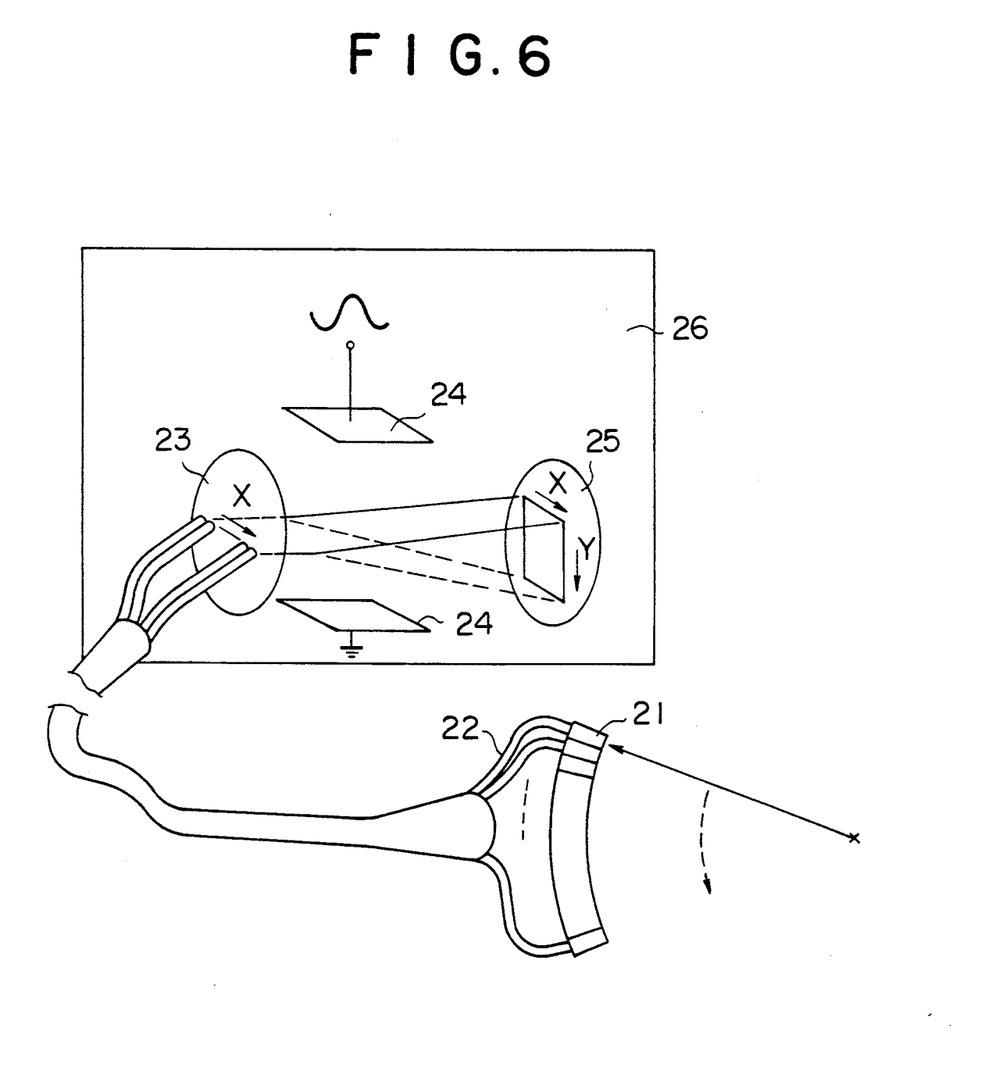
FIG. 6 is a conceptual view showing an optical detector according to another embodiment.
Figure 7A:
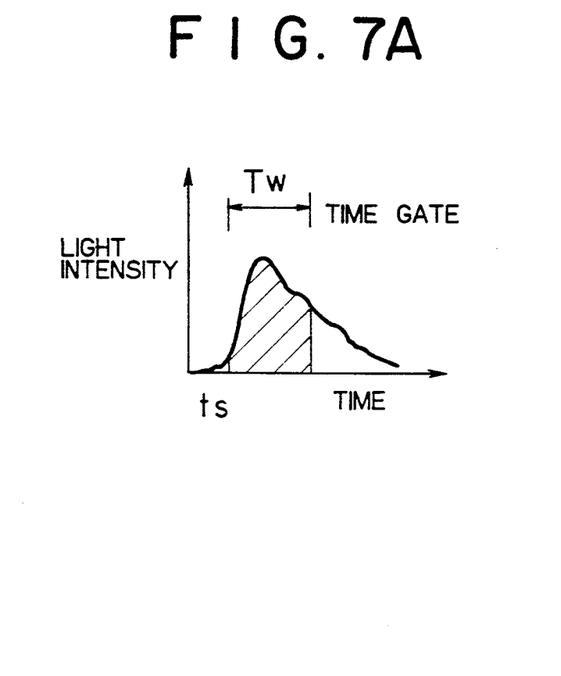
FIGS. 7A and 7B are waveform views showing a function of the optical detector shown in FIG. 6.
Figure 7B:
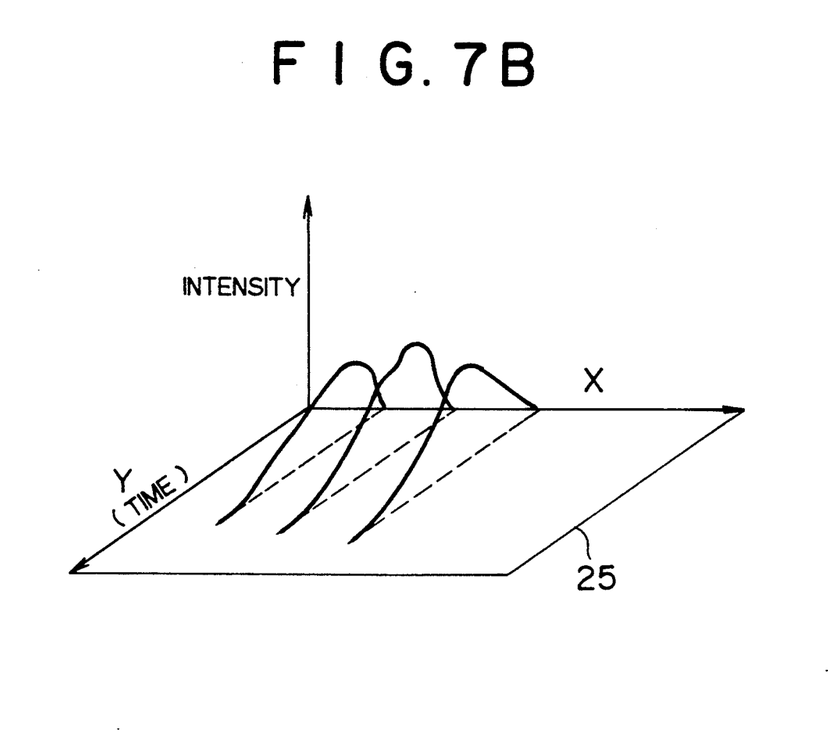

FIGS. 6, 7A, and 7B show the construction of an optical detector and its function according to another embodiment. For implementing the time gate function without using the light shutter, it is necessary to employ as an optical detector an apparatus for analyzing and recording time-based variation of light quantity (referred to as an optical time spectrum) in picosecond. According to this embodiment shown in FIG. 6, light reception window arrays 21 arranged in an arch state are provided on the gantry 17 in place of the light shutter 3 and the optical detector 2 shown in FIG. 1. One light reception window matches to one element of the optical detector 2 in FIG. 1. Each of the windows is connected to an optical fiber. The other ends of the optical fibers 22 are connected near an optical cathode 23 of streak camera 26 in a manner that they are arranged in a constant interval along the x direction. Each time the light pulse is radiated, it reaches each light reception window and then enters into the corresponding spot of the optical cathode 23. Hence, at each radiation of a light pulse, the transmitted light received at each window is transformed to electronic beams and these beams are fired to an anode 25. A high-frequency deflected voltage is applied onto a deflecting electrode 25 of the streak camera 26 thereby sweeping each electronic beam in the Y direction. That is, the time-based variation of quantity of light as shown in FIG. 7A is transformed into the Y-directed distribution of the electrons fired to the anode 25. The anode 25 contains a fluorescent material coated thereon. The coat serves to reserve the strength of the electronic beams as luminous strength for a given time. However, for one pulse radiation, the anode 25 serves to reserve for a short time a two-dimensional light strength distribution indicating the light time spectrum at each light-spectacle window. The light strength distribution is imaged by a TV camera, for example, and is recorded in memory, which is included in the data acquisition system 6. Of the recorded data, only the data corresponding to a hatching portion of FIG. 7A is depicted for realizing a time gate of a time width $T_w$.

The apparatus according to this embodiment, therefore, makes it possible to carry out that measurement at each radiation of the two light pulses of respective wavelengths using the streak camera 26, record the resulting optical time spectrum, and calculate an integrated value of data within a predetermined time gate. The overall measuring process is repeated as a radiating angle of the beams is changing, thereby the projection data being provided like the foregoing embodiment. The process of image reconstruction is similar to that of the foregoing embodiment.

The above-mentioned embodiments having described that the light beams are radiated in a manner to depict a fan, the light beams may be moved in parallel. Further, it may be possible to employ the construction wherein the optical detecting elements (or light reception windows) are disposed around an object. On the construction, only the beam-radiating spot (position of the mirror) is moved for obtaining pieces of projection data without moving the optical detecting elements. And, using polarized beams as a light source and a deflection filter in front of the optical detector (light-receptacle window), it is possible to lessen the adverse effect resulting from light scattering more. In addition, it is to be noted that various modifications may be made.

We claim:

1. A method for optically inspecting a human body to be inspected comprising the steps of:
   a) radiating a first light pulse of a first wavelength from a radiating spot to said human body and detecting the first light pulse transmitted through said human body at least at a specific light-reception spot, said first wavelength being selected within a wavelength range from a visible wavelength to an infrared wavelength and being overlapped with an absorption wavelength band specific to metabolic materials contained in said human body to be inspected;
   b) radiating a second light pulse of a second wavelength from said radiating spot to said human body to be inspected and detecting the second light pulse transmitted through said human body at least at said specific light-reception spot, said second wavelength being close to said first wavelength so that light attenuation due to light scattering in said human body to be inspected utilizing said second wavelength is substantially the same as light attenuation due to light scattering in said human body to be inspected utilizing said first wavelength;
   c) respectively extracting integrated values of light pulse transmission at said first and second wavelengths detected at least at said light-reception spot within a specific time gate;
   d) computing a ratio of said integrated value of the light pulse transmission at said first wavelength to that of the light pulse transmission at said second wavelength;
   e) iteratively executing said steps a), b), c), and d) as said radiating spot and said light-radiating spot are changed in succession, for obtaining pieces of projection data from said ratio of integrated values being successively provided; and
   f) reconstructing an image bout distribution of absorbed light in said human body from said pieces of projection data.

2. The method as set forth in claim 1 wherein said time gate width is wider than the pulse width of said first and second light pulses.

3. The method as set forth in claim 1 wherein the gate width of said time gate is defined according to a light path width to be restricted.

4. The method as set forth in claim 1 wherein said time gate is required to be opened on such a timing as having a time lag behind the pulse leading edge of said each light pulse.

5. The method as set forth in claim 1 wherein said time gate is implemented by opening or shutting a light shutter provided on said each light-receptacle spot.

6. The method as set forth in claim 1 wherein said first and second light pulse transmissions are transformed into electronic beams, said electronic beams are swept as time passes, and the resulting beams are recorded as a distribution of intensity of said electronic beams.

7. A method for optically inspecting a human body to be inspected comprising the steps of:
   a) radiating a first light pulse of a first wavelength from a radiating spot to said human body and detecting within a first time gate the first light pulse transmitted through said human body at at least a specific light-receptacle spots, said first wavelength being selected within a wavelength range from a visible wavelength to an infrared wavelength and being overlapped with an absorption wavelength band specific to metabolic materials in said human body to be inspected b) radiating a second light pulse of a second wavelength from said radiating spot to said human body to be inspected and detecting within a second time gate the second light pulse transmitted through said human body at least at said specific light-reception spot, said second wavelength being close to said first wavelength so that light attenuation due to light scattering in said human body to be inspected utilizing said second wavelength is substantially the same as light attenuation due to light scattering in said human body to be inspected utilizing said first wavelength;

c) respectively extracting integrated values of light pulse transmission at said first and second wavelengths detected at least at said light-reception spot;

d) computing a ratio of said integrated value of the light pulse transmission at said first wavelength to said integrated value of the light pulse transmission at said second wavelength;

e) iteratively executing said steps a(, b), c), and d) as said radiating spot and said light-reception spot are changed in succession, for obtaining pieces of projection data from said ratio of integrated values being successively provided; and f) reconstructing an image bout distribution of absorbed light in said human body from said pieces of projection data.

8. The method as set forth in claim 7 wherein said first and second time gate widths are wider than the pulse widths of said first and second light pulses.

9. The method as set forth in claim 7 wherein said first and second time gates are defined according to a light path width to be restricted.

10. The method as set forth in claim 7 wherein said first and second time gates are required to be opened on such a timing as having a time lag behind the leading edge of said each light pulse.

11. A method for optically inspecting a human boy to be inspected comprising the steps of:

a) radiating a first light pulse of a first wavelength from a radiation spot to said human body, said first wavelength being selected within a wavelength range from a visible wavelength to an infrared wavelength and being overlapped with an absorption wavelength band specific to metabolic materials contained in said human body to be inspected;

b) detecting said first light pulse transmitted through said human body at least at a specific light-reception spot, transforming said first light pulse detected at least at said light-reception spot into an electronic beam, electrically sweeping said electronic beam as time passes, recording a first optical time spectrum indicating the time change of light transmission at said first wavelength;

c) radiating a second light pulse of a second wavelength from said radiation spot to said human body to be inspected, said second wavelength being close to said first wavelength so that light attenuation due to light scattering in said human body to be inspected utilizing said second wavelength is substantially the same as light attenuation due to light scattering in said human body to be inspected utilizing said first wavelength;

e) detecting said second light pulse transmitted through said human body at least at said specific light-reception spot, transforming said second light pulse detected at least at said light reception spot into an electronic beam, electrically sweeping said electronic beams as time passes, and recording a second optical time spectrum indicating the time change of said light transmission at said second wavelength;

f) integrating each signal of said first and second optical time spectrum with time gates, and computing a ratio of both integrated values;

g) integrating each signal of said first and second optical time spectrums with time gates, and computing a ratio of both integrated values;

h) iteratively executing said steps a), b), c), and d) as said radiating spot and at least said light-reception spot are changed in succession, for obtaining pieces of projection data from said ratio of integrated values being successively provided; and i) reconstructing an image bout distribution of absorbed light in said human body from said pieces of projection data.

12. The method as set forth in claim 11 wherein said time gate widths are wider than the pulse widths of said first and second light pulses.

13. The method as set forth in claim 11 wherein said time gates are defined according to a light path width to be restricted.

14. A method for optically inspecting a human body comprising the steps of:

a) fixing said body to be inspected and measuring and recording an outer shape of a predetermined section thereof;

b) radiation a first light pulse of a first wavelength to said human body to be inspected from a specific radiating spot on said section, said first wavelength being selected within a wavelength range from a visible wavelength to an infrared wavelength and being overlapped with an absorption wavelength band specific to metabolic materials contained in said human body, and measuring the first light pulse transmitted through said human body at least at a specific light-reception spot on said section;

c) radiating a second light pulse at a second wavelength from said radiation spot to said human body, said second wavelength being close to said first wavelength so that light attenuation due to light scattering in said human body to be inspected utilizing said second wavelength is substantially the same as light attenuation due to light scattering in said human body to be inspected utilizing said first wavelength, and measuring said second light pulse transmitted through said human body at least at said light reception spot;

d) extracting an integrated value of light pulse transmission at said first wavelength residing within a first time gate having a specific width, said first time gate being opened in a manner to have a time lag behind the leading edge of said first light pulse, said time lag being defined according to a light path length in the human body, and said light path length being defined on said outer shape;

e) extracting an integrated value of light pulse transmission at said second wavelength residing within a second time gate having a specific width, said second time gate being opened in a manner to lag behind the leading edge of said second light pulse;

f) deriving a ratio of said integrated value of the light pulse transmission at said first wavelength to that of the light pulse transmission at said second wavelength;

g) iteratively executing said steps b), c), d), e), and f) as said radiating spot and at least said light-reception spot are changing on said section, for obtaining pieces of projection data based on said ratio being being successively derived; and h) reconstructing an image about distribution of light absorption on said section of said human body from said pieces of projection data.

15. The method as set forth in claim 14, wherein said outer shape is measured by scanning a light beam on said section and obtaining projections of said human body at said section.

16. An apparatus for optically inspecting a human body comprising:

light-radiating means for alternately radiating to said human body to be inspected a first light pulse of a first wavelength, said first wavelength being selected within a wavelength range from a visible wavelength to an infrared wavelength and being overlapped with an absorption wavelength band specific to metabolic materials contained in said human body, and a second light pulse of a second wavelength being close to said first wavelength so that light attenuation due to light scattering in said human body to be inspected utilizing said second wavelength is substantially the same as light attenuation due to light scattering in said human body to be inspected utilizing said first wavelength;

scanning mans for changing direction of radiation for each combination of radiation of said first and second light pulses;

an optical detector means for serially detecting said first and second light pulses transmitted through said human body;

time gate means for restricting said first and second light pulses output at sad optical detector means; and data-processing means for deriving a ratio of an integrated value o said detected light pulse transmission at said first wavelength to that of said detected light pulse transmission at said second wavelength for each of angles a direction of radiation to provide projection data about said human body from said projection data.

* * * * *